United States Patent
Gong et al.

(10) Patent No.: US 10,211,957 B2
(45) Date of Patent: Feb. 19, 2019

(54) METHOD AND SYSTEM FOR SIMULTANEOUS INFORMATION AND ENERGY TRANSFER WITH A GUARD INTERVAL SIGNAL

(71) Applicant: South University of Science and Technology of China, Guangdong (CN)

(72) Inventors: Yi Gong, Guangdong (CN); Zidong Han, Guangdong (CN); Yue Zhang, Guangdong (CN); Xiaoyang Li, Guangdong (CN); Mingzhe Li, Guangdong (CN)

(73) Assignee: SOUTH UNIVERSITY OF SCIENCE & TECHNOLOGY OF CHINA, Guangdong (CN)

( * ) Notice: Subject to any disclaimer, the term of this patent is extended or adjusted under 35 U.S.C. 154(b) by 0 days.

(21) Appl. No.: 15/831,072

(22) Filed: Dec. 4, 2017

(65) Prior Publication Data

US 2018/0091271 A1 Mar. 29, 2018

Related U.S. Application Data

(63) Continuation of application No. PCT/CN2015/086139, filed on Aug. 5, 2015.

(30) Foreign Application Priority Data

Jul. 21, 2015 (CN) .......................... 2015 1 0432211

(51) Int. Cl.
*H04L 5/00* (2006.01)
*H02J 50/00* (2016.01)
(Continued)

(52) U.S. Cl.
CPC ............ *H04L 5/0044* (2013.01); *H02J 50/00* (2016.02); *H02J 50/20* (2016.02);
(Continued)

(58) Field of Classification Search
CPC ............... H04L 5/0044; H04L 27/2626; H04L 27/2647; H04L 27/2605; H02J 50/20; H02J 7/025; H02J 7/0068
See application file for complete search history.

(56) References Cited

U.S. PATENT DOCUMENTS

2007/0258394 A1* 11/2007 Hamaguchi ........... H04L 5/0044
370/310
2015/0229133 A1* 8/2015 Reynolds ............ H04W 52/281
307/24
(Continued)

FOREIGN PATENT DOCUMENTS

CN 104135454 A 11/2014
CN 104320471 A 1/2015
(Continued)

OTHER PUBLICATIONS

A. A. Nasir, X. Zhou, S. Durrani and R. A. Kennedy, "Relaying Protocols for Wireless Energy Harvesting and Information Processing," in IEEE Transactions on Wireless Communications, vol. 12, No. 7, pp. 3622-3636, Jul. 2013.*
K. Huang and X. Zhou, "Cutting the last wires for mobile communications by microwave power transfer," in IEEE Communications Magazine, vol. 53, No. 6, pp. 86-93, Jun. 2015.*
(Continued)

*Primary Examiner* — Sam K Ahn
*Assistant Examiner* — Amneet Singh
(74) *Attorney, Agent, or Firm* — Myers Wolin, LLC

(57) ABSTRACT

A simultaneous information and energy transfer method and system with a guard interval signal are provided. The method comprises the steps of generating, by a transmitting terminal, a controllable guard interval signal according to the current energy demand and environment conditions for channel transmission. The system comprises a transmitting terminal configured to generate a controllable guard interval
(Continued)

signal. In the system and method, the guard interval time is fully utilized to transfer a guard interval signal with controllable amount of energy, which not only prevents intersymbol interference, but also provides controllable energy signals within the guard interval time at the same time, thus improving the energy transfer performance of the system and reducing the probability that the receiving terminal is unable to operate normally due to energy shortage. The present invention can be widely applied to a variety of simultaneous wireless information and energy transfer systems.

5 Claims, 1 Drawing Sheet

(51) Int. Cl.
*H02J 50/20* (2016.01)
*H04L 27/26* (2006.01)
(52) U.S. Cl.
CPC ...... *H04L 27/2605* (2013.01); *H04L 27/2626* (2013.01); *H04L 27/2646* (2013.01); *H04L 27/2647* (2013.01)

(56) References Cited

U.S. PATENT DOCUMENTS

| | | | |
|---|---|---|---|
| 2015/0303741 A1* | 10/2015 | Malik | H04B 5/0037 307/104 |
| 2016/0285519 A1 | 9/2016 | Gong Yi | |
| 2017/0358943 A1* | 12/2017 | Bocus | H02J 7/025 |

FOREIGN PATENT DOCUMENTS

| | | |
|---|---|---|
| CN | 104734832 A | 6/2015 |
| CN | 104812078 A | 7/2015 |
| CN | 104836765 A | 8/2015 |
| WO | 2014044149 A1 | 3/2014 |
| WO | 2016149948 A1 | 9/2016 |
| WO | 2016149949 A1 | 9/2016 |

OTHER PUBLICATIONS

International Search Report, dated Apr. 26, 2016, for corresponding international application PCT/CN2015/086139.

* cited by examiner

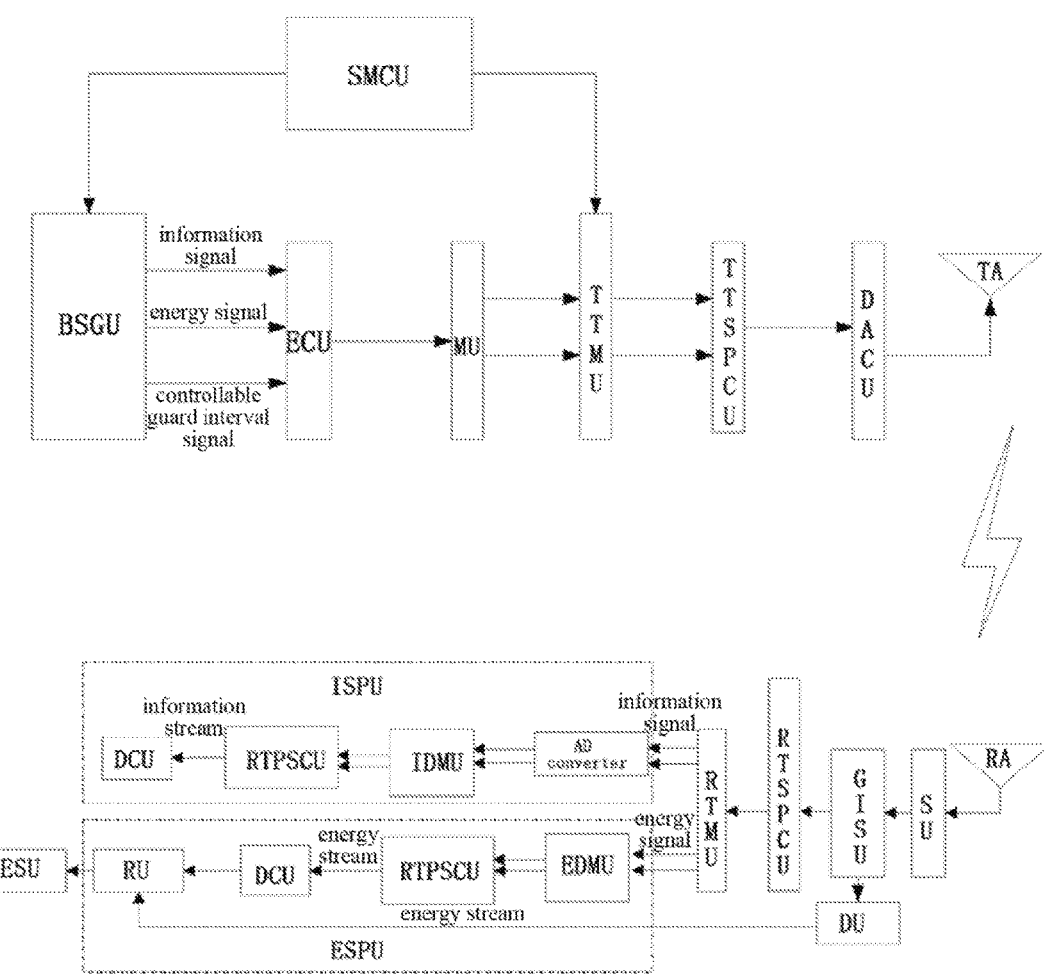

METHOD AND SYSTEM FOR SIMULTANEOUS INFORMATION AND ENERGY TRANSFER WITH A GUARD INTERVAL SIGNAL

CROSS REFERENCE TO RELATED APPLICATIONS

This application is a continuation under 35 U.S.C. § 120 of International Application PCT/CN2015/086139, filed Aug. 5, 2015, which claims priority to Chinese Application 201510432211.7, filed Jul. 21, 2015, the contents of each of which are incorporated by reference herein.

FIELD OF THE INVENTION

The present invention relates to an intersection of the wireless communication technology and the wireless power transmission technology, and in particular to a method and system for simultaneous information and energy transfer.

BACKGROUND

The simultaneous wireless information and energy transfer (i.e., simultaneous transfer of information and energy in a wireless mode) is a new communication technology integrating the wireless communication technology and the wireless energy transmission technology. With the development of science and technology, the integration of the energy technology and the communication technology becomes a trend, which can not only realize a high-speed and reliable communication, but also effectively ease the pressure on scarcity of energy and spectrum, thereby having important application value in industry, medical treatment, infrastructure development, etc.

The simultaneous wireless information and energy transfer breaks through the traditional wireless communication means, takes energy attributes into consideration at the same time and integrates the wireless communication technology with the wireless energy transfer technology, thus enabling a parallel and simultaneous transfer of information and energy and having wide application value and innovation significance.

The simultaneous information and energy transfer may be used in various wireless terminals or devices which rely on batteries of limited capacity for power supply based on its characteristics, and feed the wireless terminals or devices by harvesting energy from signals, thereby greatly prolonging the standby time, decreasing the device volume and cost, and reducing the battery throughput significantly. Therefore, the environmental pollution caused during manufacture and recycling of batteries is greatly reduced. Based on the characteristics of non-contact long-distance transmission, the power supplied by batteries or cables can be replaced, and the convenience of the power supply is greatly improved. Based on the characteristics of stability and sustainability, the conventional way of harvesting environmental energy (such as wind energy, solar energy and kinetic energy) by energy harvesters can be replaced. Meanwhile, the simultaneous wireless information and energy transfer is widely applied in the improvement of people's life and brings about great social benefits. In the medical field, there is a serious problem of shortage of battery energy in implanting medical devices such as cardiac pacemakers and cardiovascular robots, the assembly of the simultaneous wireless information and energy transfer technology can protect patients form severe secondary pains.

In the application documents "TRANSMITTING SYSTEM AND RECEIVING SYSTEM FOR MULTICARRIER BROADBAND SIMULTANEOUS INFORMATION AND ENERGY TRANSFER" (Application No. 201510133784.X), "TRANSMITTING METHOD AND RECEIVING METHOD FOR SIMULTANEOUS INFORMATION AND ENERGY TRANSFER" (Application No. 201510133428.8) and "MULTICARRIER BROADBAND SIMULTANEOUS INFORMATION AND ENERGY TRANSFER OPTIMIZATION METHOD" (Application No. 201510133789.2), the inventor(s) has (have) proposed a simultaneous information and energy transfer method, wherein baseband signals transmitted by the system contain information baseband signals and energy baseband signals, which are both simultaneously transmitted after being processed correspondingly, and sufficient electric energy is provided to a receiving terminal through the energy signals. The method can be widely applied in the digital communication and analog communication.

In a simultaneous information and energy transfer system, in order to eliminate the intersymbol interference, a guard interval is inserted between each signal symbol to prevent intersymbol interference. The above simultaneous information and energy transfer system has the following two drawbacks:

First, since useful signals cannot be transmitted during the time of a guard interval, time resources of this interval may not be fully utilized, causing waste of resources and degrading the system performance at the same time; and Second, since a receiving terminal of the simultaneous information and energy transfer system can only acquire energy from energy signals, in case that the receiving terminal requires an additional energy source, the system is unable to configure or provide the additional energy source flexibly.

SUMMARY

To solve the above technical problems, the present disclosure aims to provide a simultaneous information and energy transfer method which can not only prevent intersymbol interference, but also provide an additional energy source dynamically for a receiving terminal.

To solve the above technical problems, another object of the present disclosure is to provide a simultaneous information and energy transfer system which can not only prevent intersymbol interference, but also provide an additional energy source dynamically for a receiving terminal.

The technical solution adopted is as follows.

A method for simultaneous wireless information and energy transfer with a guard interval signal, which is applied to a simultaneous information and energy transfer system, the system comprising:

a transmitting terminal transmitting a baseband signal comprising an information signal, an energy signal and a controllable guard interval signal, and a receiving terminal, the method comprising the steps of:

S1, generating, by the transmitting terminal, a controllable guard interval signal according to current energy demand and channel environment conditions for—transmission;

S2, processing and transmitting, by the transmitting terminal, the information signal, the energy signal and the controllable guard interval signal to the receiving terminal;

S3, receiving and processing, by the receiving terminal, the signals transmitted by the transmitting terminal; and S4, harvesting, by the receiving terminal, energy in the energy signal and/or energy in the controllable guard interval signal of the signals transmitted by the transmitting terminal.

Preferably, in step S1, the current energy demand of the receiving terminal is specifically an energy-storage operating mode energy demand or a normal operating mode energy demand, and the controllable guard interval signal is associated with control of the following parameters: time length and/or carrier allocation and/or power allocation of the guard interval signal; the step S1 specifically comprises the sub-steps of:

S11, generating, by the transmitting terminal, a controllable guard interval signal with larger energy when the receiving terminal is in the energy-storage operating mode; and S12, generating, by the transmitting terminal, a controllable guard interval signal with smaller energy or a controllable guard interval signal having identifying meaning when the receiving terminal is in the normal operating mode.

Preferably, further comprising the step of:

S5, providing, by the receiving terminal, electric energy required for the current operating mode of the receiving terminal by utilizing the energy in the energy signal and/or the energy in the controllable guard interval signal harvested.

Preferably, the step S2 is specifically: performing, by the transmitting terminal, encoding, serial-parallel conversion, shunting, modulation, parallel-serial conversion and digital-to-analog conversion on the information signal, the energy signal and the controllable guard interval signal, and transmitting the serial simultaneous information and energy transfer analog signal to the receiving terminal.

Preferably, the step S3 specifically comprises the sub-steps of:

S31, receiving, by the receiving terminal, and converting the serial simultaneous information and energy transfer analog signal into a parallel simultaneous information and energy transfer analog signal;

S32, determining whether the serial simultaneous information and energy transfer signal within a guard interval is a controllable guard interval signal containing energy; if yes, harvesting the guard interval signal within the guard interval and rectifying and storing the signal into an energy storage unit (ESU);

S33, shunting an information analog signal and an energy analog signal in the parallel simultaneous information and energy transfer analog signal;

S34, performing analog-to-digital conversion on the information analog signal to obtain an information digital signal, and performing information demodulation, parallel-serial conversion and decoding on the information digital signal in a digital domain; and S35, processing and then storing the energy analog signal into the energy storage unit.

A system for simultaneous wireless information and energy transfer with guard interval signal, wherein it is used for implementing the method for simultaneous wireless information and energy transfer with guard interval signal, the system comprising:

a transmitting terminal configured to generate a guard interval signal with corresponding energy according to an operating mode of a receiving terminal, and process and then transmit an information signal, an energy signal and a controllable guard interval signal to the receiving terminal; and a receiving terminal configured to receive and process the signals transmitted by the transmitting terminal, and harvest the energy in the energy signal and/or the energy in the controllable guard interval signal of the signals transmitted by the transmitting terminal.

Preferably, the transmitting terminal comprises a baseband signal generation unit (BSGU) configured to generate the controllable guard interval signal according to current energy demand and channel environment conditions for transmission.

Preferably, the transmitting terminal further comprises:

an encoding unit (ECU) configured to perform encoding of the information baseband signal, the energy baseband signal and the controllable guard interval signal respectively to generate corresponding baseband encodings;

a transmitting terminal serial-parallel conversion unit (TTSPCU) configured to perform serial-parallel conversion on a baseband encoding signal to generate a parallel data stream;

a transmitting terminal mapping unit (TTMU) configured to classify the parallel data stream and perform corresponding modulation and pre-allocation to the information baseband signal, the energy baseband signal and the controllable guard interval signal in the parallel data stream according to a pre-allocation parameter set;

a modulation unit (MU) configured to modulate the information baseband signal, the energy baseband signal and the controllable guard interval signal in the parallel data stream onto pre-allocated subcarriers according to results of the modulation and pre-allocation;

a transmitting terminal parallel-serial conversion unit configured to convert the parallel data stream into a serial data stream;

a digital-to-analog conversion unit (DACU) configured to convert the serial data stream into simultaneous information and energy transfer analog signal and send the signal into a transmitting antenna (TA); and a transmitting antenna configured to transmit the serial simultaneous information and energy transfer analog signal;

the receiving terminal further comprises:

a receiving antenna (RA) configured to receive the serial simultaneous information and energy transfer analog signal;

a guard interval separation unit (GISU) configured to separate the controllable guard interval analog signal from the serial simultaneous information and energy transfer analog signal;

a receiving terminal serial-parallel conversion unit (RTSPCU) configured to convert the serial simultaneous information and energy transfer analog signal into parallel simultaneous information and energy transfer analog signal;

a receiving terminal mapping unit (RTMU) configured to shunt the information analog signal and the energy analog signal in the parallel simultaneous information and energy transfer analog signal;

an information signal processing unit (ISPU) configured to perform analog-to-digital conversion on the information analog signal to obtain an information digital signal, and perform information demodulation, parallel-serial conversion and decoding on the information digital signal in the digital domain;

an energy signal processing unit (ESPU) configured to preprocess the energy analog signal in the analogy domain and then store the signal into the energy storage unit; and an energy storage unit configured to store energy.

Preferably, the information signal processing unit comprises an analog-to-digital conversion unit, an information demodulation unit (IDMU), a receiving terminal parallel-serial conversion unit (RTPSCU) and a decoding unit (DCU) connected sequentially.

Preferably, the energy signal processing unit comprises an energy demodulation unit (EDMU), a parallel-serial conversion unit, a decoding unit and a rectification unit (RU) connected sequentially.

The present system and method have the beneficial effects that:

in the present system and method, the guard interval time is fully utilized to transfer a controllable guard interval signal, which not only prevents the intersymbol interference, but also provides a controllable energy signal within the guard interval time at the same time, thus improving the energy transfer performance of the system and reducing the probability that the receiving terminal is unable to operate normally due to energy shortage.

The present disclosure can be widely applied to a variety of simultaneous wireless information and energy transfer systems.

BRIEF DESCRIPTION OF THE DRAWINGS

Specific implementations of the present invention will be further described in detail with reference to the accompanying drawings, in which:

FIG. 1 is a structural block diagram of an embodiment of a circuit of a simultaneous information and energy transfer system of the present disclosure.

DETAILED DESCRIPTION OF THE PREFERRED EMBODIMENTS

It should be noted that the embodiments of the present application and the features of the embodiments may be combined without conflicting with each other.

Provided is a method for simultaneous wireless information and energy transfer with a guard interval signal, which is applied to a simultaneous information and energy transfer system, the system comprising:
a transmitting terminal transmitting a baseband signal comprising an information signal, an energy signal and a controllable guard interval signal, and
a receiving terminal,
the method comprising the steps of:
S1, generating, by the transmitting terminal, a controllable guard interval signal according to current energy demand and channel environment conditions for transmission;
S2, processing and transmitting, by the transmitting terminal, the information signal, the energy signal and the controllable guard interval signal to the receiving terminal;
S3, receiving and processing, by the receiving terminal, the signals transmitted by the transmitting terminal; and
S4, harvesting, by the receiving terminal, energy in the energy signal and/or energy in the controllable guard interval signal of the signals transmitted by the transmitting terminal;
S5, providing, by the receiving terminal, electric energy required for the current operating mode of the receiving terminal by utilizing the energy in the energy signal and/or the energy in the controllable guard interval signal harvested.

The electric energy required for the current operating mode of the receiving terminal may be additional electric energy required for charging, or electric energy required for maintenance of the receiving and processing operation of the receiving terminal. When the receiving terminal is in a normal operating mode, an energy-storage operating mode or a power-consuming operating mode (the receiving terminal needs to speed up power consumption), the transmitting terminal may generate a controllable guard interval signal matched therewith according to the energy demand of respective operating modes. The controllable guard interval signal is associated with the control of parameters such as the symbol energy carried by the guard interval signal, the time length of the guard interval signal, etc. Specifically, the controllable guard interval signal is associated with the control of the following parameters: the time length and/or carrier allocation and/or power allocation of the guard interval signal, etc. In step S1, the channel environment conditions for transmission refer to the parameters such as signal intensity varying in strength, varying transmission efficiency due to the time variability of the wireless channel.

In this embodiment, in step S1, the current energy demand of the receiving terminal specifically refers to the energy demand in the energy-storage operating mode or the normal operating mode. Of course, the energy demands in other operating modes are also included, for example the energy demand in an energy-consuming mode, etc. The controllable guard interval signal corresponds to an additional energy source provided for the receiving terminal, which provides matching energy for the receiving terminal according to the actual need of the receiving terminal. Specifically, the step S1 comprises the sub-steps of: S11, generating, by the transmitting terminal, a controllable guard interval signal with larger energy when the receiving terminal is in the energy-storage operating mode; and S12, generating, by the transmitting terminal, a controllable guard interval signal with smaller energy or a controllable guard interval signal having identifying meaning when the receiving terminal is in the normal operating mode. It is noted that the guard interval signal with larger energy and the guard interval signal with smaller energy are relative terms, and the transmitting terminal may control and generate a guard interval signal matched with the receiving terminal according to the current operating mode (electric energy demand) of the receiving terminal.

Preferably, the step S2 is specifically: performing, by the transmitting terminal, encoding, serial-parallel conversion, shunting, modulation, parallel-serial conversion and digital-to-analog conversion on the information signal, the energy signal and the controllable guard interval signal, and transmits the serial simultaneous information and energy transfer analog signal to the receiving terminal.

Preferably, the step S3 specifically comprises the following sub-steps of: S31, receiving, by the receiving terminal, and converting the serial simultaneous information and energy transfer analog signal into a parallel simultaneous information and energy transfer analog signal; S32, determining whether the serial simultaneous information and energy transfer signal within a guard interval is a controllable guard interval signal containing energy; if yes, harvesting the guard interval signal within the guard interval and rectifying and storing the signal into an energy storage unit; S33, shunting an information analog signal and an energy analog signal in the parallel simultaneous information and energy transfer analog signal; S34, performing analog-to-digital conversion on the information analog signal to obtain an information digital signal, and performing information demodulation, parallel-serial conversion and decoding on the information digital signal in a digital domain; and S35, preprocessing the energy analog signal in an analogy domain and storing the processed signal into the energy storage unit.

A system for simultaneous wireless information and energy transfer with a guard interval signal, which is used for implementing a method for simultaneous wireless information and energy transfer with a guard interval signal, and comprises: a transmitting terminal configured to generate a guard interval signal with corresponding energy according to an operating mode of a receiving terminal, and process and then transmit an information signal, an energy signal and a controllable guard interval signal to the receiving terminal; and the receiving terminal configured to receive and process the signals transmitted by the transmitting terminal, and harvest the energy in the energy signal and/or the energy in the controllable guard interval signal of the signals transmitted by the transmitting terminal.

Preferably, the transmitting terminal comprises a baseband signal generation unit configured to acquire the current energy demand of the receiving terminal and the channel environment conditions for transmission, and generate a controllable guard interval signal according to the current energy demand and channel environment conditions for transmission.

Preferably, the transmitting terminal further comprises: an encoding unit configured to perform encoding to an information baseband signal, an energy baseband signal and a controllable guard interval signal respectively to generate corresponding baseband encodings; a transmitting terminal serial-parallel conversion unit configured to perform serial-parallel conversion on a baseband encoding signal to generate a parallel data stream; a transmitting terminal mapping unit configured to classify the parallel data stream and perform corresponding modulation and pre-allocation to the information baseband signal, the energy baseband signal and the controllable guard interval signal in the parallel data stream according to a pre-allocation parameter set; a modulation unit configured to modulate the information baseband signal, the energy baseband signal and the controllable guard interval signal in the parallel data stream onto pre-allocated subcarriers according to results of the modulation and pre-allocation; a transmitting terminal parallel-serial conversion unit configured to convert the parallel data stream into a serial data stream; a digital-to-analog conversion unit configured to convert the serial data stream into simultaneous information and energy transfer analog signal and send the signal into a transmitting antenna; and the transmitting antenna configured to transmit the serial simultaneous information and energy transfer analog signal. The receiving terminal further comprises: a receiving antenna configured to receive the serial simultaneous information and energy transfer analog signal; a guard interval separation unit configured to separate the controllable guard interval analog signal from the serial simultaneous information and energy transfer analog signal; a receiving terminal serial-parallel conversion unit configured to convert the serial simultaneous information and energy transfer analog signal into parallel simultaneous information and energy transfer analog signal; a receiving terminal mapping unit configured to shunt the information analog signal and the energy analog signal in the parallel simultaneous information and energy transfer analog signal; an information signal processing unit configured to perform analog-to-digital conversion on the information analog signal to obtain an information digital signal, and perform information demodulation, parallel-serial conversion and decoding on the information digital signal in the digital domain; an energy signal processing unit configured to preprocess the energy analog signal in the analogy domain and then store the signal into the energy storage unit; and the energy storage unit configured to store energy.

Preferably, the information signal processing unit comprises an analog-to-digital conversion unit, an information demodulation unit, a receiving terminal parallel-serial conversion unit and a decoding unit connected sequentially.

Preferably, the energy signal processing unit comprises an energy demodulation unit, a parallel-serial conversion unit, a decoding unit and a rectification unit connected sequentially.

FIG. 1 is a schematic structural view of a specific embodiment of the simultaneous wireless information and energy transfer system of the present disclosure.

In this specific embodiment, the transmitting terminal further comprises a signal management and control unit (SMCU) configured to match an optimization algorithm based on the current energy demand of the receiving terminal and channel quality parameters, perform pre-allocation of the carriers, power and spectrum to the information signal data stream, the energy signal data stream and the controllable guard interval signal data stream in the baseband signal dynamically, and generate a pre-allocation parameter set to the baseband signal generation unit and the transmitting terminal mapping unit. The baseband signal generation unit is configured to generate the information signal and the energy signal, and generate the guard interval signal with controllable amount of energy according to the current operating mode of the receiving terminal. The information signal, the energy signal and the guard interval signal are sequentially subjected to encoding by the encoding unit, serial-parallel conversion by the transmitting terminal serial-parallel conversion unit, shunting by the transmitting terminal mapping unit, modulation by the modulator, parallel-serial conversion by the transmitting terminal parallel-serial conversion unit and digital-to-analog conversion by the digital-to-analog conversion unit, and then form a serial simultaneous information and energy transfer analog signal which is transmitted to the receiving terminal by the transmitting antenna.

The receiving antenna of the receiving terminal receives the serial simultaneous information and energy transfer analog signal. A synchronization unit (SU) is configured to enable the serial signal received to maintain phase synchronization with the transmitting terminal. The serial simultaneous information and energy transfer analog signal processed by the synchronization unit is then subjected to guard interval separation by the guard interval separation unit. A determination unit (DU) is configured to determine whether a signal within the guard interval of the serial simultaneous information and energy transfer signal contains the energy signal; if yes, the energy signal within the guard interval is harvested and sent to the rectification unit for rectification and then stored into the energy storage unit. The signal in an effective interval of the serial simultaneous information and energy transfer analog signal is separated by the guard interval separation unit and then is subjected to serial-parallel conversion by the receiving terminal serial-parallel conversion unit to obtain the parallel simultaneous information and energy transfer analog signal. The information analog signal and the energy analog signal in the parallel simultaneous information and energy transfer analog signal are shunted by the receiving terminal mapping unit. After being subjected to analog-to-digital conversion by the analog-to-digital conversion unit in the signal processing unit, the information analog signal is subjected to corresponding signal processing in the digital domain. The energy analog signal is processed by an energy processing unit in the analogy domain and then stored into the energy storage unit.

In the present system and method, the guard interval time is fully utilized to transfer a guard interval signal controllable in amount of energy, which not only prevents the intersymbol interference, but also provides controllable energy signals within the guard interval time at the same time, thus improving the energy transfer performance of the system and reducing the probability that the receiving terminal is unable to operate normally due to energy shortage. The present disclosure can be widely applied to a variety of simultaneous information and energy transfer system.

Preferred embodiments of the present invention have been described above, but the present invention is not limited thereto. Numerous equivalent variations and substitutions may be made by those skilled in the art without departing from the spirit of the invention and should all fall within the scope defined by the claims of the present application.

What is claimed is:

1. A method for simultaneous wireless information and energy transfer with a guard interval signal, which is applied to a simultaneous information and energy transfer system, the system comprising:
    a transmitting terminal transmitting a baseband signal comprising an information signal, an energy signal and a controllable guard interval signal, and
    a receiving terminal,
    the method comprising the steps of:
    S1, generating, by the transmitting terminal, a controllable guard interval signal according to current energy demand and environment conditions for channel transmission;
    S2, processing and transmitting, by the transmitting terminal, the information signal, the energy signal and the controllable guard interval signal to the receiving terminal;
    S3, receiving and processing, by the receiving terminal, the signals transmitted by the transmitting terminal; and
    wherein the step S2 further comprises performing, by the transmitting terminal, encoding, serial-parallel conversion, shunting, modulation, parallel-serial conversion and digital-to-analog conversion on the information signal, the energy signal and the controllable guard interval signal, and transmitting the serial simultaneous information and energy transfer analog signal to the receiving terminal; and
    wherein, the step S3 specifically comprises the sub-steps of:
    S31, receiving, by the receiving terminal, and converting the serial simultaneous information and energy transfer analog signal into a parallel simultaneous information and energy transfer analog signal;
    S32, determining whether the serial simultaneous information and energy transfer signal within a guard interval is a controllable guard interval signal containing energy; if yes, harvesting the guard interval signal within the guard interval and rectifying and storing the signal into an energy storage unit;
    S33, shunting an information analog signal and an energy analog signal in the parallel simultaneous information and energy transfer analog signal;
    S34, performing analog-to-digital conversion on the information analog signal to obtain an information digital signal, and performing information demodulation, parallel-serial conversion and decoding on the information digital signal in a digital domain; and
    S35, processing and then storing the energy analog signal into the energy storage unit, by sequentially energy demodulating, parallel-serial converting, decoding and rectifying the energy analog signal.

2. The method for simultaneous wireless information and energy transfer with a guard interval signal of claim 1, wherein in step S1, the current energy demand of the receiving terminal is specifically an energy demand of an energy-storage operating mode or a normal operating mode, and the controllable guard interval signal is associated with control of the following parameters: time length or carrier allocation or power allocation of the guard interval signal; the step S1 further comprising the sub-steps of:
    S11, generating, by the transmitting terminal, a controllable guard interval signal with larger energy when the receiving terminal is in the energy-storage operating mode; and
    S12, generating, by the transmitting terminal, a controllable guard interval signal with smaller energy or only a controllable guard interval signal having identifying meaning when the receiving terminal is in the normal operating mode.

3. The method for simultaneous wireless information and energy transfer with a guard interval signal of claim 2, further comprising the step of:
    S5, providing, by the receiving terminal, electric energy required for the current operating mode of the receiving terminal by utilizing the energy in the energy signal or the energy in the controllable guard interval signal harvested.

4. A system for simultaneous wireless information and energy transfer with a guard interval signal, the system comprising:
    a transmitting terminal configured to generate a guard interval signal with corresponding energy according to an operating mode of a receiving terminal, and process and then transmit an information signal, an energy signal and a controllable guard interval signal to the receiving terminal; and
    a receiving terminal configured to receive and process the signals transmitted by the transmitting terminal, and harvest the energy in the energy signal or the energy in the controllable guard interval signal of the signals transmitted by the transmitting terminal;
    wherein the transmitting terminal comprises:
    an encoding circuit configured to perform encoding to the information baseband signal, the energy baseband signal and the controllable guard interval signal respectively to generate corresponding baseband encodings;
    a transmitting terminal serial-parallel conversion circuit configured to perform serial-parallel conversion on a baseband encoding signal to generate a parallel data stream;
    a transmitting terminal mapping circuit configured to classify the parallel data stream and perform corresponding modulation and pre-allocation to the information baseband signal, the energy baseband signal and the controllable guard interval signal in the parallel data stream according to a pre-allocation parameter set;
    a modulation circuit configured to modulate the information baseband signal, the energy baseband signal and the controllable guard interval signal in the parallel data stream onto pre-allocated subcarriers according to results of the modulation and pre-allocation;

a transmitting terminal parallel-serial conversion circuit configured to convert the parallel data stream into a serial data stream;

a digital-to-analog conversion circuit configured to convert the serial data stream into simultaneous information and energy transfer analog signal and send the signal into a transmitting antenna;

a transmitting antenna configured to transmit the serial simultaneous information and energy transfer analog signal, and a baseband signal generation circuit configured to generate the controllable guard interval signal according to current energy demand and environment conditions for channel transmission;

wherein, the receiving terminal further comprises:

a receiving antenna configured to receive the serial simultaneous information and energy transfer analog signal;

a guard interval separation circuit configured to separate the controllable guard interval analog signal from the serial simultaneous information and energy transfer analog signal;

a receiving terminal serial-parallel conversion circuit configured to convert the serial simultaneous information and energy transfer analog signal into parallel simultaneous information and energy transfer analog signal;

a receiving terminal mapping circuit configured to shunt the information analog signal and the energy analog signal in the parallel simultaneous information and energy transfer analog signal;

an information signal processing circuit configured to perform analog-to-digital conversion on the information analog signal to obtain an information digital signal, and perform information demodulation, parallel-serial conversion and decoding on the information digital signal in the digital domain; and an energy signal processing circuit configured to preprocess the energy analog signal in the analog domain and then store the signal into an energy storage circuit configured to store the energy, wherein the energy signal processing circuit comprises an energy demodulation circuit, a parallel-serial conversion circuit, a decoding circuit and a rectification circuit connected sequentially.

5. The system for simultaneous wireless information and energy transfer with a guard interval signal of claim 4, wherein the information signal processing circuit comprises an analog-to-digital conversion circuit, an information demodulation circuit, a receiving terminal parallel-serial conversion circuit and a decoding circuit connected sequentially.

\* \* \* \* \*